United States Patent [19]
Tooley et al.

[11] Patent Number: 5,874,221
[45] Date of Patent: Feb. 23, 1999

[54] SPECIES SPECIFIC METHOD FOR THE PCR DETECTION OF PHYTHOPHTHORA

[75] Inventors: Paul Tooley; Britt Bunyard, both of Frederick; Marie Carras, Myersville; Efstathios Hatziloukas, Frederick, all of Md.

[73] Assignee: The United States of America as represented by the Secretary of Agriculture, Washington, D.C.

[21] Appl. No.: 704,207

[22] Filed: Aug. 28, 1996

[51] Int. Cl.$^6$ .......................... C12P 19/34; C07H 21/04; C07H 21/00
[52] U.S. Cl. .......................... 435/6; 435/91.2; 536/22.1; 536/24.3; 536/25.3; 536/24.33
[58] Field of Search ..................... 435/6, 91.2; 536/22.1, 536/24.3, 25.3, 24.33

[56] References Cited

FOREIGN PATENT DOCUMENTS 9529260  11/1995  WIPO .

OTHER PUBLICATIONS

Ersek et al., "PCR Amplification of Species–Specific DNA Sequences Can Distinguish Among Phytophthora Species", Applied and Environmental Microbiology, vol. 60(7), pp. 2616–2621, Jul. 1994.

Niepold et al., "Application of the PCR Technique to Detect *Phytophthora infestans* in Potato Tubers and Leaves", Microbiol. Res., vol. 150, pp. 379–385, 1995. (Only Abstract).

Niepold et al. Application of the PCR technique to detect *phytophthora infestans* in potato tubers and leaves. Microbiological Research vol. 150(4), pp. 379–385. (Only Abstract), 1995.

O'Donnell Ribosomal DNA internal transcribed spacers are highly divergent in the phytopathogenic ascomycete Fusarium sambucinum. Curr. Genet. vol. 22, pp. 213–220, 1992.

Wildman et al. Studies on the secondary structure of 5.8S rRNA from a Thermophile, Thermomyces Ianuginosus. J. Biol. Chemistry. vol. 256, pp. 5675–5682, 1981.

Tooley et al. Development of PCR primers from internal transcribed spacer region 2 for detection of Phytophthora species infecting potatoes. Applied and Environmental Microbiology, vol. 63(4), pp. 1467–1475, 1997.

Database search Accession NO: Y08674 and Y08670, 1997.

*Primary Examiner*—Kenneth R. Horlick
*Assistant Examiner*—Joyce Tung
*Attorney, Agent, or Firm*—M. Howard Silverstein; John Fado; Janelle S. Graeter

[57] ABSTRACT

*Phytophthora* species which infect potatoes may result in the devastating disease potato late blight or in pink rot. Primers specific for *Phytophthora infestans* (late blight), and for *Phytophthora erythroseptica* and *Phytophthora nicotianae* (pink rot) have been designed which are useful for detecting the presence of the microorganisms by polymerase chain reaction methods. The primers were derived from the internal transcribed spacer region of *Phytophthora* ribosomal DNA and may be used to confirm the presence of the microorganisms or to distinguish among them.

10 Claims, 8 Drawing Sheets

SPECIES SPECIFIC METHOD FOR THE PCR DETECTION OF PHYTHOPHTHORA

BACKGROUND OF THE INVENTION

1. Field of the Invention

Phytophthora is a fungal plant pathogen which causes devastating diseases of potatoes, including late-blight disease. This disease occurs in potato plants in the field as well as in storage. Fungicides have been utilized to control the pathogen, however, new strains have become resistant, resulting in extensive crop loss. This invention relates to novel primers which can be used to detect pathogenic Phytophthora species and to distinguish among the pathogenic species.

2. Description of the Relevant Art

Potato late blight caused by Phytophthora infestans (P. infestans) has become extremely severe in recent years due to the influx of a new more variable pathogen population. Extensive crop loss from late blight disease has occurred in many areas of the U.S. and Canada with the occurrance of both foliar destruction and the rotting of blighted tubers in storage. Often, tubers which are asymptomatic but contain latent P. infestans infection are placed in storage and are eventually partially or totally lost as infections develop and are exacerbated by secondary infection with other pathogens such as Erwinia carotovora subsp. carotovora (bacterial soft rot). A rapid, accurate test is thus needed to identify Phytophthora species in the field, in harvested tubers and in seedlots to determine levels of infection and to detect the pathogen when no visible symptoms occur. This enables growers to decide whether to harvest a crop or to declare it a loss. Results of such a test may also dictate the control measures a grower may invoke early in the season to control late blight, as well as provide confirmatory data about the presence of pathogens in seedlots which could affect certification and/or sale. Such a test is also needed to identify the specific organisms present in the tubers, i.e. to differentiate late blight from other tuber diseases such as pink rot and Pythium leak.

Microbiological and immunological assays as well as visual examinations have conventionally been utilized for detecting the presence of Phytophthora species in infested samples. However, these methods have suffered from an inability to clearly distinguish one species from another. For example, potato late blight infection can easily be confused with pink rot, and misdiagnoses may occur which could cause improper acceptance or rejection of seedlots during seed certification.

Various molecular approaches have been used to differentiate Phytophthora species, including use of random genomic fragments (Goodwin et al. 1989. Phytopathology. vol. 79, pp. 716–721; Goodwin et al. 1990. Appl. Environ. Micro. vol. 56, pp. 669–674), mitochondrial DNA (Förster et al. 1988. Mycologia. vol. 80, pp. 466–478; Förster et al. 1990. Exper. Mycol. vol. 14, pp. 18–31) and ribosomal DNA (Lee and Taylor. 1992. Mol. Biol. Evol. vol. 9, pp. 636–653; Lee et al. 1993. Phytopathology. vol. 83, pp. 177–181). For detection, tests based on the polymerase chain reaction (PCR) are the most rapid and sensitive available, and amplification by PCR for Phytophthora detection has been carried out by various investigators. Érsek et al. (1994. Applied and Environmental Microbiology. vol. 60, no. 7, pp. 2616–2621), for example, have reported amplification of DNA from P. parasitica and P. citrophthora with species-specific primers, and Niepold and Schöber-Butin (1995. Microbiological Research. vol. 150, pp. 379–385) have disclosed primers derived from the repetitive sequence of P. infestans which were effective for detecting that species. In addition, a PCR-based detection method has been described for the raspberry root rot fungus P. fragariae var. rubi based on a highly repetitive fragment containing the small subunit ribosomal RNA gene (Stammler and Seemüller. 1993. Z. Pflanzen. Pflanzenschutz. vol. 100, pp. 394–400).

The search has continued, however, for additional primers which are useful in a rapid and sensitive assay for the detection of the pathogen and for distinguishing between species of Phytophthora which are potato pathogens.

SUMMARY OF THE INVENTION

We have discovered oligonucleotide sequences which are capable of amplifying DNA fragments specific for several species of Phytophthora potato pathogens by PCR. The primers can be used to confirm the presence of potato late blight in potato tissue and to distinguish among the organisms causing potato late blight and pink rot in tubers.

In accordance with this discovery, it is an object of the invention to provide the novel oligonucleotides for use as primers for PCR assays for the specific detection and identification of Phytophthora infestans (P. infestans), Phytophthora erythroseptica (P. erythroseptica) and Phytophthora nicotianae (P. nicotianae).

It is also an object of the invention to provide a PCR assay method utilizing the novel primers.

Other objects and advantages of the invention will become readily apparent from the following description.

Figure 1A:
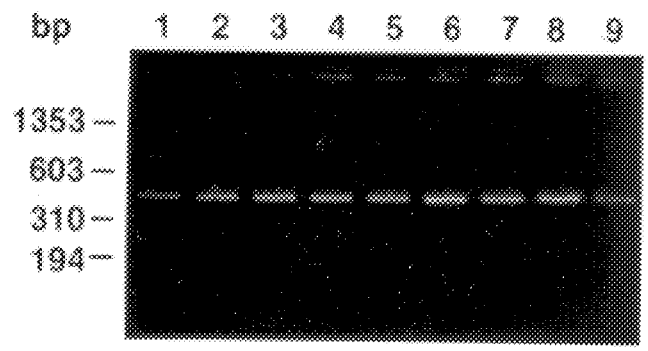
FIG. 1 shows the PCR amplification of DNA from eighteen Phytophthora infestans isolates using P. infestans primer set PINF2/ITS3. Lanes 1–9 (FIG. 1a) represent isolates 568, 519, 179, 135, 575, 181, 127, 111 and 178, respectively. Lanes 10–18 (FIG. 1b) represent isolates 618, 580, 180, 550, 561, 1103, 177, 543 and 510, respectively.

nicotianae 361 (lane 4), P. mirabilis 340 (lane 5), P. ilicis 343 (lane 6), P. hibernalis 337 (lane 7), P. colocasiae 345 (lane 8), P. cryptogea 310 (lane 9), P. phaseoli 330 (lane 10), Fusarium oxysporum FS1 (lane 11), Pythium ultimum PY4 (lane 12) and negative DNA control (lane 13).

Figure 4A:
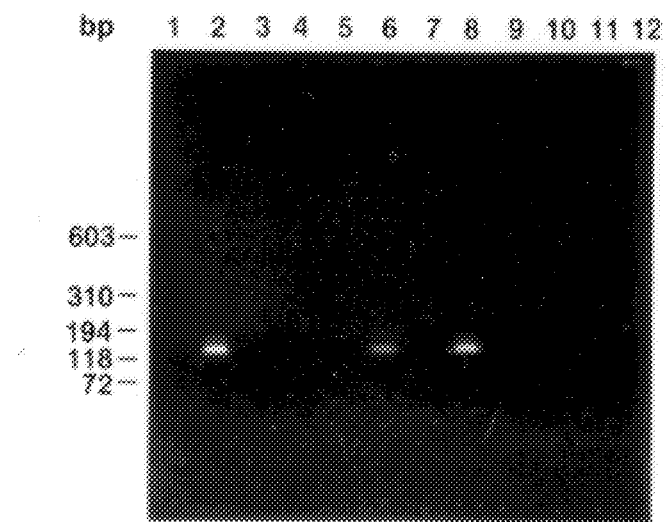
Figure 4B:
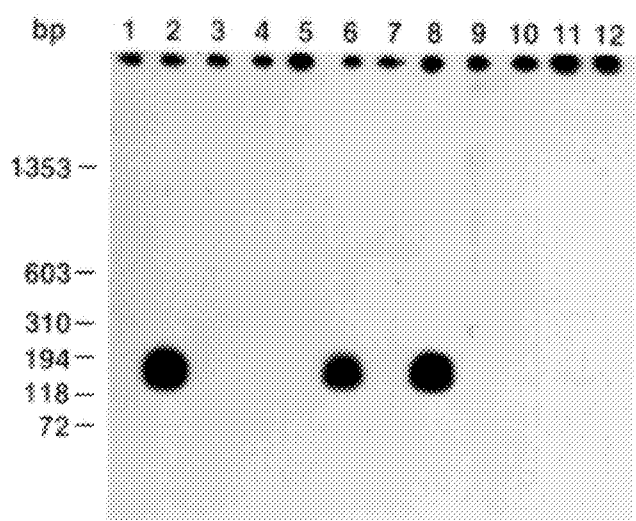

FIG. 4 shows the PCR amplification of DNA from various Phytophthora species, Fusarium oxysporum and Pythium ultimum isolated from infected potatoes and using P. erythroseptica primer set PERY2/ITS4. The product, 10 µl from a 25-µl reaction, was electrophoresed on a 2% agarose gel for 1.5 h at 100 V, followed by staining with ethidium bromide (FIG. 4a) and Southern hybridization (FIG. 4b) with labeled plasmid pT7Blue T-vector containing the cloned ITS2 region from P. infestans isolate 580 (B). Lanes 1–12 represent P. infestans 580 (lane 1), P. erythroseptica 366 (lane 2), P. nicotianae 361 (lane 3), P. mirabilis 340 (lane 4), P. ilicis 343 (lane 5), P. hibernalis 337 (lane 6), P. colocasiae 346 (lane 7), P. cryptogea 310 (lane 8), P. phaseoli 330 (lane 9), Fusarium oxysporum FS1 (lane 10), Pythium ultimum PY4 (lane 11) and negative DNA control (lane 12).

Figure 5:
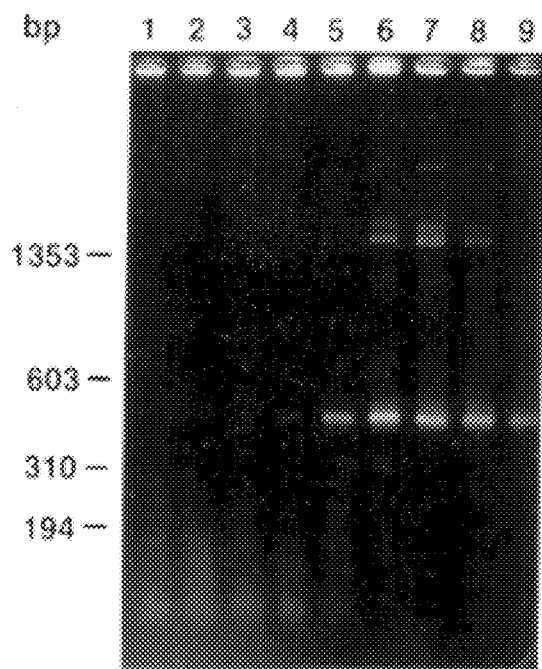

FIG. 5 shows the PCR amplification of template DNA dilution series of Phytophthora infestans (isolate 580) using primer set PINF2/ITS3. Lanes 1–9 represent negative DNA control, 100 fg DNA, 1 pg DNA, 10 pg DNA, 100 pg DNA, 1 ng DNA, 10 ng DNA, 85 ng DNA and 850 ng DNA, respectively. The observed lower limit of starting template DNA for which a PCR product could be detected was 10 pg DNA (or 1 pg DNA by Southern hybridization).

Figure 6A:
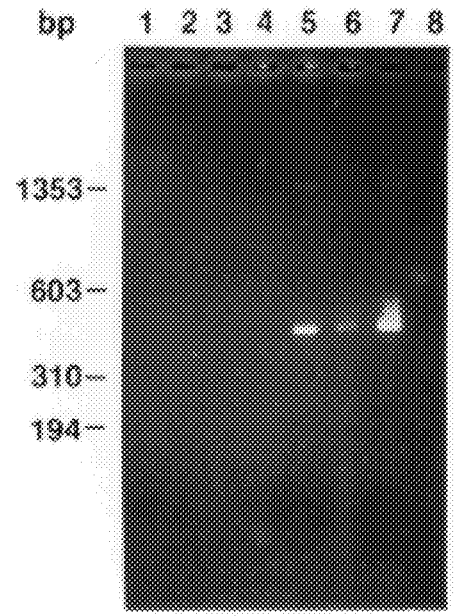
Figure 6B:
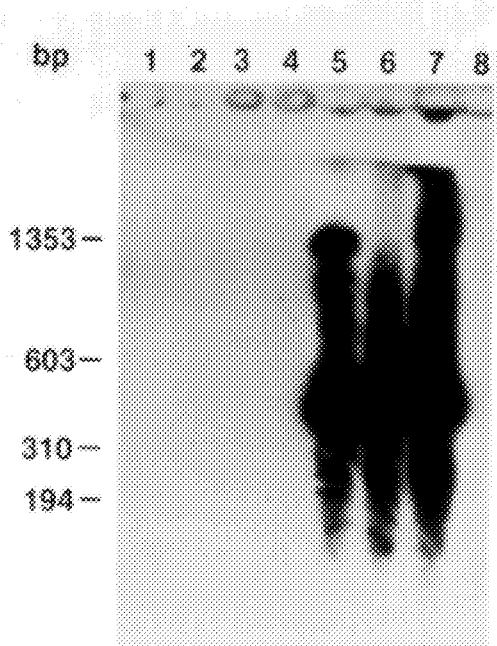

FIG. 6 shows the PCR detection of Phytophthora infestans from infected potato leaf tissue and surface of infected tuber using P. infestans primer set PINF2/ITS3. Lanes 1–7 represent potato DNA (10 ng; lane 1), negative DNA control (lane 2), empty lane (lane 3), yellowed potato leaf tissue next to late blight lesion (lane 4), water-soaked tissue area at lesion margin (lane 5), hyphae growing from surface of infected tuber (lane 6) and positive P. infestans isolate 176 DNA control (10 ng; lane 7). The product, 10 µl from a 25-µl reaction, was electrophoresed on a 2% agarose gel for 1.5 h at 100 V, followed by staining with ethidium bromide (FIG. 6a) and Southern hybridization (FIG. 6b) with labeled plasmid containing the cloned ITS2 region from P. infestans isolate 176.

Figure 7A:
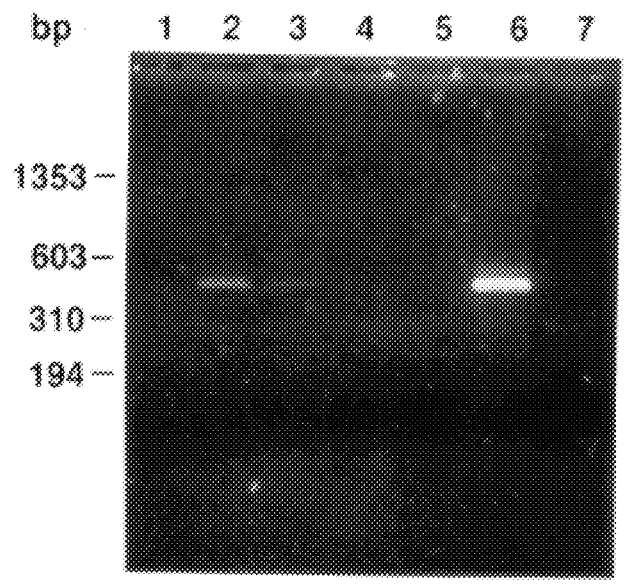
Figure 7B:
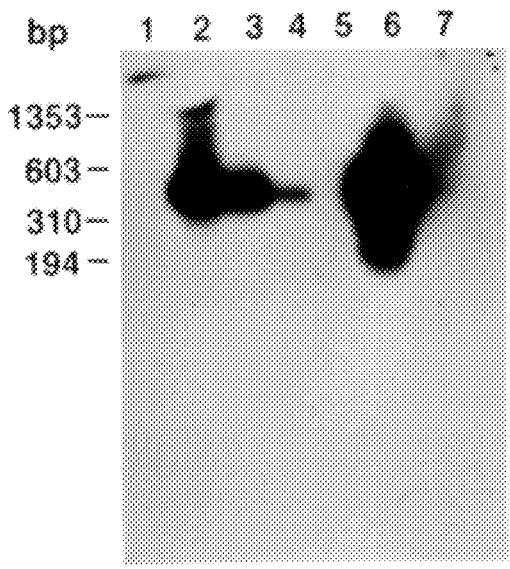

FIG. 7 shows the PCR detection of P. infestans from infected potato tuber tissue using rapid NaOH extraction method and P. infestans primer set PINF2/ITS3. The product was electrophoresed on a 2% agarose gel for 1.5 h at 100V, followed by staining with ethidium bromide (FIG. 7a) and Southern hybridization with labeled plasmid containing the cloned ITS2 region from P. infestans isolate 580 (FIG. 7b). Lane 1, 0.2 ng vector; lane 2, tissue from late blight tuber lesion; lane 3, tissue from margin of tuber lesion; lane 4, white tuber tissue from near lesion, apparently uninfected; lane 5, uninoculated potato tissue; lane 6, positive DNA control; lane 7, negative DNA control.

Figure 8A:
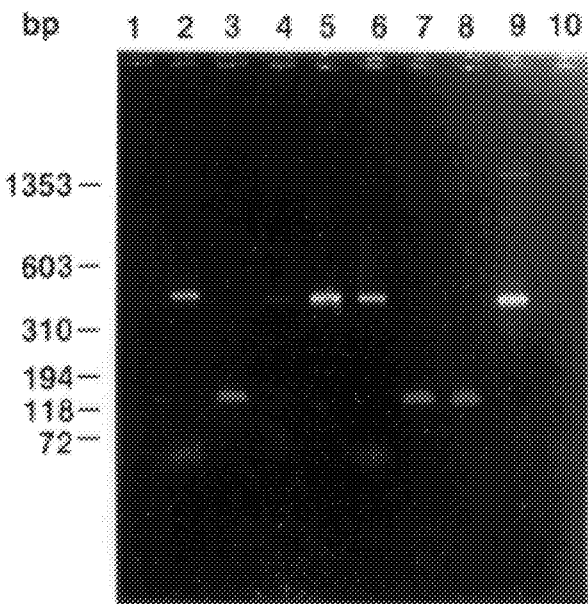
Figure 8B:
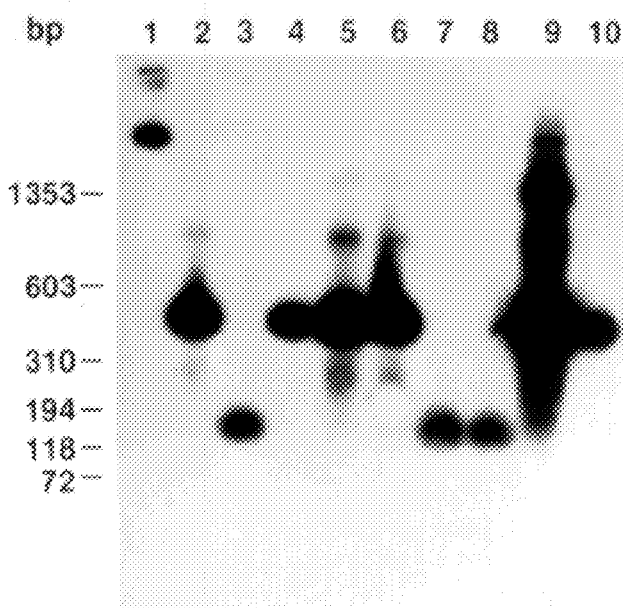

FIG. 8 shows the detection of P. infestans, P. erythroseptica and P. nicotianae from singly and multiply-infected potato tubers using modified QIAGEN extraction procedure. Inoculated tubers were incubated at 18° C. in darkness for 14 days. PCR products were detected by ethidium bromide staining (FIG. 8a) and Southern hybridization (FIG. 8b). Lane 1, 0.1 ng pT7Blue T-vector control; lane 2, potato infected with all three Phytophthora species, only P. infestans detected using P. infestans primer set PINF2/ITS3; lane 3, multiply-infected potato and P. erythroseptica primer set PERY2/ITS 4, detecting only P. erythroseptica; lane 4, multiply-infected potato and P. nicotianae primer set PNIC1/ITS3, detecting only P. nicotianae; lane 4, P. nicotianae primers PNIC1/ITS3 used to detect P. nicotianae from tuber infected only with P. nicotianae; lane 6, P. nicotianae positive DNA control (10 ng); lane 7, P. erythroseptica primers PERY1/ITS4 used to detect P. erythroseptica from tuber infected only with P. erythroseptica; lane 8, P. erythroseptica positive control DNA (10 ng); lane 9, P. infestans primers PINF2/ITS3 used to detect P. infestans from tuber infected only with P. infestans; lane 10, P. infestans positive control DNA (10 ng).

DETAILED DESCRIPTION OF THE INVENTION

Tests based on DNA sequences and PCR are the most rapid and sensitive available to date and can lend themselves to large sample throughput. PCR primers were thus developed to amplify DNA fragments specific for several species of Phytophthora pathogenic to potatoes.

PCR primers were designed based on DNA sequence analysis of the internal transcribed spacer region (ITS2) of ribosomal DNA from Phytophthora, Pythium and Fusarium species which infect potato tubers. The primers can specifically detect P. infestans in leaf and tuber tissue and thereby differentiate late blight from pink rot, which is caused by P. erythroseptica and P. nicotianae, as well as from Pythium and Fusarium species isolated from infected tubers.

The ITS2 region of ribosomal DNA was reported to contain a substantial amount of restriction site variation among the different Phytophthora species in taxonomic Group IV (Falkenstein et al. 1991. Phytopathology. vol. 81, pp. 1157). This region was therefore targeted as a possible source of DNA which would be specific for the different species. DNA was extracted from fungal isolates (Table 1), and the ITS2 region was amplified by PCR using primers ITS3 and ITS4 (described by White et al. 1990. In PCR Protocols. Innis et al., eds. Academic Press, San Diego, Calif., pp. 315–322). The PCR products were cloned into the pT7Blue

TABLE I

Isolates of Phytophthora species and other fungi and bacteria used in this study.

| Species and isolate | Source | Origin | Year isolated |
|---|---|---|---|
| Phytophthora infestans | | | |
| 111 (ATCC 48720)[a] | 1[b] | Albany Co., NY | 1983 |
| 127 (ATCC 48723) | 1 | Spencerport, NY | 1982 |
| 135 (ATCC 52009) | 1 | Portage Co., WI | 1983 |
| 176 (Deahl 915) | 2[c] | Athens, PA | 1987 |

TABLE I-continued

Isolates of Phytophthora species and other fungi and bacteria used in this study.

| Species and isolate | Source | Origin | Year isolated |
|---|---|---|---|
| 177 (Deahl 917) | 2 | Vancouver, BC | 1989 |
| 178 (Deahl W719) | 2 | Blaine, BC | 1991 |
| 179 (Deahl W720) | 2 | Blaine, BC | 1991 |
| 180 (Deahl WW-1X) | 2 | Mt. Vernon, WA | 1991 |
| 181 (Deahl WW-1AE) | 2 | Mt. Vernon, WA | 1991 |
| 510 | 1 | Toluca, Mexico | 1983 |
| 519 (ATCC 64091) | 1 | Toluca, Mexico | 1983 |
| 543 | 1 | La Puerta, Mexico | 1983 |
| 550 (ATCC 64095) | 1 | Tenango, Mexico | 1983 |
| 561 | 1 | Chapingo, Mexico | 1984 |
| 568 | 1 | Chapingo, Mexico | 1984 |
| 580 | 1 | Toluca, Mexico | 1986 |
| 618 | 1 | Toluca, Mexico | 1987 |
| 1103 | 1 | Renkum, The Netherlands | 1984 |
| *Phytophthora erythroseptica* | | | |
| 355 (Lambert LAQ) | 3[d] | Presque Isle, ME | 1993 |
| 356 (Lambert AN) | 3 | Caribou, ME | 1993 |
| 357 (Lambert Ni-2) | 3 | Ft. Fairfield, ME | 1993 |
| 358 (Lambert Af-1) | 3 | Presque Isle, ME | 1993 |
| 365 (Mulrooney 109) | 4[e] | Park Rapids, MN | 1992 |
| 366 (ATCC 36302) | 5[f] | Ohio | 1975 |
| 367 (Goodwin A) | 1 | Steuben Co., NY | 1994 |
| 368 (Goodwin B) | 1 | Steuben Co., NY | 1994 |
| 369 (Goodwin C) | 1 | Steuben Co., NY | 1994 |
| *Phytophthora nicotianae* | | | |
| 359 (Mulrooney Fairview #4) | 6[g] | Townsend, DE | 1993 |
| 360 (Mulrooney Fairview #8) | 6 | Townsend, DE | 1993 |
| 361 (Mulrooney Wicks #2) | 6 | Townsend, DE | 1993 |
| 362 (Mulrooney Wicks #8) | 6 | Townsend, DE | 1993 |
| 363 (Mulrooney Bergold #3) | 6 | Milford, DE | 1993 |
| 364 (Mulrooney Bergold #5) | 6 | Milford, DE | 1993 |
| *Phytophthora cryptogea* | | | |
| 310 (Hamm 620) | 7[h] | unknown | unknown |
| *Phytophthora colocasiae* | | | |
| 345 (Coffey P1696) | 8[i] | China | unknown |
| *Phytophthora hibernalis* | | | |
| 337 (Coffey P647) | 8 | California | unknown |
| *Phytophthora ilicis* | | | |
| 343 (Coffey P6099) | 8 | Oregon | unknown |
| *Phytophthora mirabilis* | | | |
| 340 (Coffey P3007) | 8 | Mexico | unknown |
| *Phytophthora phaseoli* | | | |
| 352 (Coffey P7626) | 8 | unknown | unknown |
| *Pythium ultimum* | | | |
| PY-4 | 3 | Presque Isle, Maine | 1994 |
| PY-5 | 3 | Presque Isle, Maine | 1994 |
| *Fusarium avenaceum* | | | |
| FS-2 | 3 | Presque Isle, Maine | 1994 |
| *Fusarium oxysporum* | | | |
| FS-1 | 3 | Presque Isle, Maine | 1994 |
| FS-8 | 9 | Wisconsin | 1991 |
| *Fusarium sambucinum* | | | |
| FS-3 | 9[j] | Idaho | 1992 |
| *Alternaria solani* | | | |
| AS-1 | 10[k] | Hastings, Florida | 1993 |
| *Helminthosporium solani* | | | |
| HS-2 | 9 | New Brunswick, Canada | 199 |
| HS-4 | 9 | North Dakota | 19 |

TABLE I-continued

Isolates of Phytophthora species and other fungi and bacteria used in this study.

| Species and isolate | Source | Origin | Year isolated |
|---|---|---|---|
| *Verticillium albo-atrum* | | | |
| VAA-1 | 10 | Minnesota | 1994 |
| *Verticillium dahliae* | | | |
| VD-1 | 10 | Minnesota | 1995 |
| *Rhizoctonia solani* | | | |
| RZ-1 | 10 | Maine | 1995 |
| Bacterial pathogens: | | | |
| *Erwinia carotovora* | | | |
| subsp. *atroseptica* | | | |
| ECA-1 | 10 | Colorado | 1990 |
| ECA-2 | 10 | Colorado | 1990 |
| subsp. *carotovora* | | | |
| ECC-1 | 10 | Colorado | 1990 |
| *Erwinia chrysanthemi* | | | |
| ECH-1 | 10 | Colorado | 1990 |
| *Pseudomonas solanacearum* | | | |
| PSOL-1 | 10 | Florida | 1993 |
| PSOL-2 | 10 | Florida | 1993 |

[a]ATCC = American Type Culture Collection accession number.
[b]1: obtained from collection of W. E. Fry, Cornell University.
[c]2: obtained from collection of Ken Deahl, Vegetable Laboratory, Beltsville, MD.
[d]3: obtained from Dave Lambert, University of Maine via Ken Deahl, Beltsville, MD.
[e]4: obtained from Bob Mulrooney, University of Delaware; originally from Neil Gudmestad, North Dakota State University.
[f]5: obtained from the American Type Culture Collection, Rockville, MD.
[g]6: isolate obtained from Bob Mulrooney, University of Delaware Mulrooney et al., 1994).
[h]7: isolate obtained from P. B. Hamm (E. M. Hansen), Oregon State University.
[i]8: isolate obtained from M. D. Coffey, University of California, Riverside. For cross-referencing purposes, Coffey P1696 = ATCC 56193; Coffey P647 = ATCC 32995; Coffey P3007 = ATCC 64070; Coffey P7626 = ATCC 60171; Coffey P6099 = Hamm 771).
[j]9: isolate obtained from N. Gudmestad, North Dakota State University.
[k]10: isolate obtained from Bob Goth, USDA-ARS, Vegetable Laboratory, Beltsville, MD. Isolates AS-1, PSOL-1 and PSOL-1 were originally obtained from D. Chilimi, Quincy, FL; isolates VAA-1 and VD-1 were originally obtained from Neil Anderson, University of Minnesota; bacterial isolates ECA-1, ECC-1, and ECH-1 were originally obtained from C. A. Ishimaru, Colorado State University; isolate ECA-2 was originally obtained from M. Harrison, Colorado State University.

T-vector (Novagen, Madison, Wis.) and sequenced by automated sequencing. The sequences were aligned, and regions of sequence dissimilarity in the ITS2 region were used to design and construct PCR primers with specificity to each organism. Sequences were obtained for four isolates of *P. infestans*, five isolates of *P. erythroseptica*, four isolates of *P. nicotianae*, and two isolates each of *Pythium* and *Fusarium* species. The primers were designed to be used in combination with either ITS3 or ITS4 and to produce PCR products ranging from about 88 bp to about 537 bp.

Figure 1B:
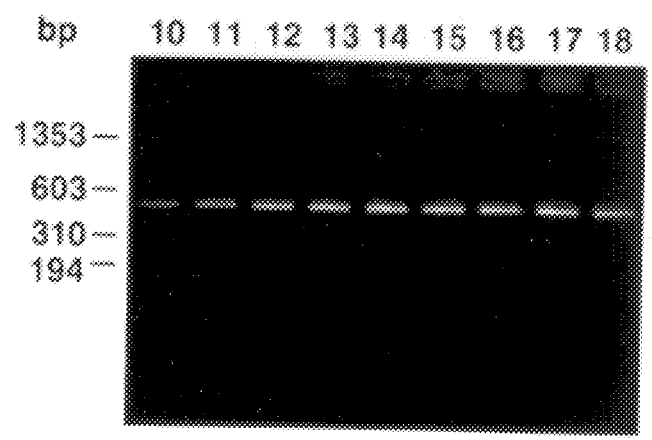

Six different primers specific for *P. infestans* were designed and were designated PINF1 to PINF6. PINF1 to PINF3 were designed for use in combination with ITS3, while PINF4 to PINF6 were for use with ITS4. Two primers specific for *P. erythroseptica* were designed and designated PERY1 and PERY2. Four primers specific for P. nicotianae were designed and designated PNIC1 to PNIC4. Using primers ITS3 and PINF2, eighteen isolates of *P. infestans* from the U.S., Mexico and Europe (Table 1, FIG. 1) were tested and reacted positively, i.e. amplifying a prominant band of the expected size (about 456 bp). No amplification was observed with six isolates of *P. nicotianae*, nine isolates of *P. erythroseptica*, two isolates of *Pythium* species and two isolates of *Fusarium* species. Primers ITS3 and PINF2 were also tested with a number of other *Phytophthora* species, and it was found that these primers also allowed amplification of ITS2 from *P. phaseoli* and *P. mirabilis*. However, while these two species are closely related to *P. infestans*, they are not pathogenic on potatoes.

Figure 2A:
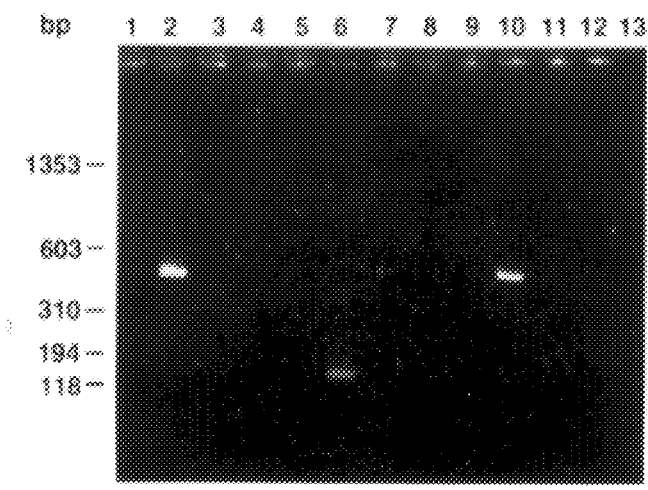
FIG. 2a shows the PCR products, (FIG. 2b) and shows Southern hybridization with three different sets of primers utilized to detect DNA of P. infestans, P. erythroseptica or P. nicotianae. The PCR product was electrophoresed on a 2% agarose gel for 1.5 h at 100 V, followed by staining with ethidium bromide (top) and Southern hybridization with labeled plasmid pT7Blue T-vector containing the cloned ITS2 region from P. infestans isolate 580 (bottom). Lanes 1–3 represent PCR reactions using P. infestans template DNA and primer sets PINF2/ITS3, PERY2/ITS4, PNIC1/ITS3, respectively; lanes 4–6 represent P. erythroseptica template DNA using the above three primer sets, respectively; and lanes 7–9 represent P. nicotianae template DNA using the above three primer sets, respectively. In each case, amplification only occurred with the primer set specific for the given species.
Figure 2B:
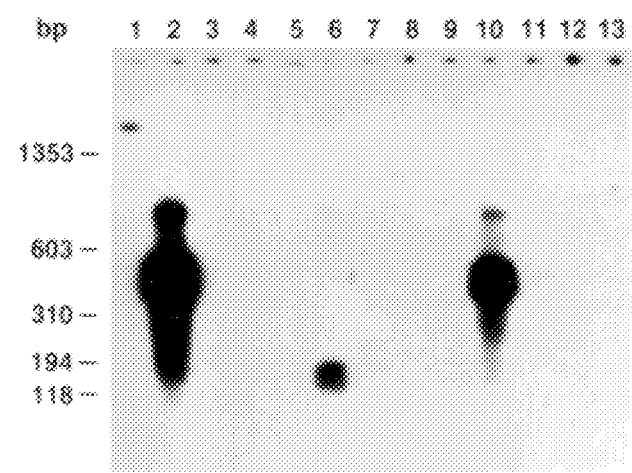

The specificity of each set of primers for the three chosen *Phytophthora* species is illustrated in FIG. 2. DNA of all three species was subjected to amplification with each of the three selected sets of primers, and amplification was only observed with the set of primers designed for the given species (FIG. 2). Results from ethidium bromide-stained agarose gels were confirmed by Southern hybridization (FIG. 2b).

The three selected sets of primers (PINF2/ITS3, PERY2/ITS4, and PNIC1/ITS3) were tested for their ability to amplify DNA from other *Phytophthora* species not known to infect potatoes, as well as DNA from other tuber-infecting fungi and bacteria. Other *Phytophthora* species tested included *P. mirabilis*, *P. phaseoli*, *P. ilicis*, *P. hibernalis*, *P. colocasiae* and *P. cryptogea* (see Table 1). Additional fungal species tested which originated from infected potatoes included *Pythium ultimum*, *Fusarium avenaceum*, *F. oxysporum*, *F. sambucinum*, *Alternaria solani*, *Helminthosporium solani*, *Verticillium albo-atrum*, *Verticillium dahliae* and *Rhizoctonia solani*. Bacterial potato pathogens tested included *Erwinia carotovora* subsp. atroseptica, *E. carotovora* subsp. *carotovora*, *E. chrysanthemi* and *Pseudomonas solanacearum* (Table 1). To verify that DNA from each of the above species was amplifiable by PCR, separate experiments were performed using primers known to amplify DNA from each species. Primers ITS3/ITS4 were used for the fungal species tested, while for bacterial species, primers R16-1/R23-2R (Nakagawa et al. 1994. *Appl. Environ. Micro.* vol. 60, pp. 637–640) and rcsA U1/L1 which amplifies a segment of the rcsA gene (Hatziloukas and Panopoulos, unpublished) were used (data not shown).

Figure 3A:
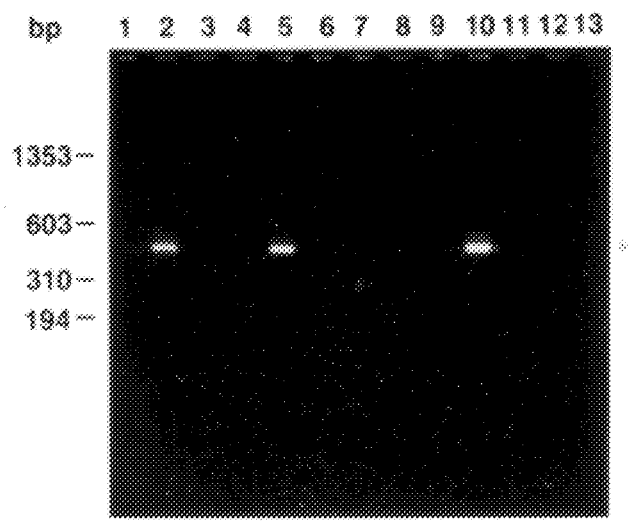
FIG. 3 shows the PCR amplification of DNA from various Phytophthora species, Fusarium oxysporum and Pythium ultimum isolated from infected potatoes and using P. infestans primer set PINF2/ITS3. The product, 10 μl from a 25-μl reaction, was electrophoresed on a 2% agarose gel for 1.5 h at 100 V, followed by staining with ethidium bromide (FIG. 3a) and Southern hybridization (FIG. 3b) with labeled plasmid pT7Blue T-vector containing the cloned ITS2 region from P. infestans isolate 580 (B). Lanes 1–13 represent 0.2 ng pT7Blue T-vector control (lane 1), P. infestans isolate 580 (lane 2), P. erythroseptica 366 (lane 3), P.
Figure 3B:
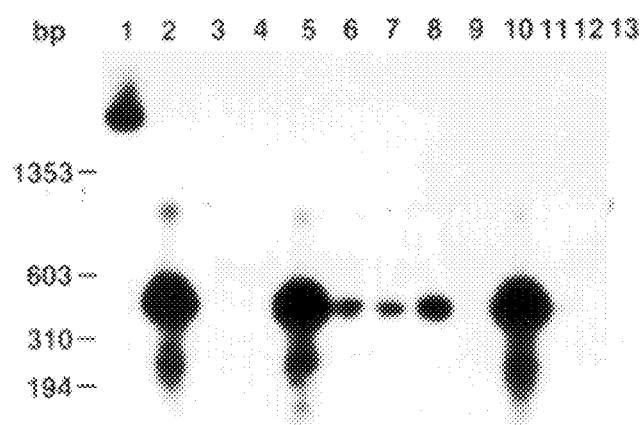

When *P. infestans* primers PINF2/ITS3 were tested for their ability to amplify DNA of other *Phytophthora* species, a high level of amplification was observed with DNA of *P. mirabilis* and *P. phaseoli*, two species very closely related to *P. infestans* taxonomically but nonpathogenic on potatoes (FIG. 3, lanes 5 and 10). Southern hybridization using the cloned ITS2 region of *P. infestans* as a probe (FIG. 3*b*, lanes 6–9) confirmed the high level of amplification observed for *P. mirabilis* and *P. phaseoli*, and also showed that a small amount of PCR product had been produced with DNA from three additional *Phytophthora* species (*P. ilicis, P. hibernalis* and *P. colocasiae*; FIG. 3, lanes 6–8). Raising the annealing temperature of the PCR reactions to 60° C. and 65° C. did not improve the specificity of the PINF2/ITS3 primers over the standard 55° C. annealing temperature, as determined by ethidium bromide-stained agarose gels and Southern hybridization (data not shown). DNA from *P. erythroseptica* (lane 3), *P. nicotianae* (lane 4), *P. cryptogea* (lane 9), *Fusarium oxysporum* (lane 11), and *Pythium ultimum* (lane 12) did not amplify using the PINF2/ITS3 primers and could not be detected by ethidium staining or Southern hybridization (FIG. 3).

To further evaluate primer specificity, experiments were performed using *P. infestans* primers PINF2/ITS3 with DNA from *P. infestans* (isolate 580), *P. erythroseptica* (366), and *P. nicotianae* (361) as well as DNA from eight other fungal pathogens of potatoes, *A. solani* (isolate AS-1), *V. alboatrum* (VAA-1), *V. dahliae* (VD-1), *R. solani* (RZ-1), *H. solani* (HS-2 and HS-4), *F. sambucinum* (FS-3) and *F. oxysporum* (FS-8). Amplification was only observed with DNA from *P. infestans*, as determined both by ethidium bromide staining of agarose gels and by Southern hybridization (data not shown).

Using *P. erythroseptica* primers PERY2/ITS4, amplification was also observed with DNA from *P. hibernalis* (FIG. 4, lane 6) and *P. cryptogea* (FIG. 4, lane 8). Results of ethidium bromide staining of agarose gels were confirmed by Southern hybridization (FIG. 4*b*).

No amplification of DNA from any other *Phytophthora* species or other fungi or bacteria was observed with *P. nicotianae* primers PNIC1/ITS3 (data not shown).

Template DNA dilutions were performed to determine the lowest amount of starting DNA that could be detected using these primers (FIG. 5). Using primers PINF2/ITS3, 10 pg of *P. infestans* DNA was detectable by ethidium bromide staining. When Southern hybridization was performed, the sensitivity level was increased to 1 pg template DNA (data not shown). Similar levels of sensitivity were obtained using primer pairs PERY2/ITS4 and PNIC1/ITS3 (data not shown).

*P. infestans*-specific primers were further tested to determine their ability to detect the pathogen in plant tissue. Healthy and infected potato tubers and leaf tissue were analyzed. Using primer pair PINF2/ITS3, *P. infestans* was detected from water-soaked tissue at foliar lesion margins and from hyphae scraped from the surface of infected tubers, but not from yellowed foliar area adjacent to lesions (FIG. 6). No amplification was observed from potato DNA (FIG. 6, lane 1).

A rapid sodium hydroxide tissue assay procedure and primer pair PINF2/ITS3 were used to detect *P. infestans* from artificially infected potato tubers (FIG. 7). Using ethidium bromide staining of agarose gels, amplification of P. infestans DNA from tuber lesion and lesion margin only were observed (FIG. 7*a*, lanes 2 and 3); however, use of Southern hybridization also allowed detection of *P. infestans* from apparently uninfected (non-discolored) tissue adjacent to tuber lesion (FIG. 7*b*, lane 4). *P. infestans* was not detected from uninoculated potato tissue (FIG. 7, lane 5).

Primer pairs PINF2/ITS3, PERY2/ITS4 and PNIC1/ITS3 were used to detect *P. infestans, P. erythroseptica* and *P. nicotianae* from tubers singly and multiply infected with the three pathogens using the modified QIAGEN method of tuber tissue assay (as described in Example 5). Using the above primers, each species could be detected from tubers singly infected with the given species. Each species could also be detected in tubers multiply infected with all three species by using the primer set designed to detect the particular species (FIG. 8). Results of ethidium bromide staining of agarose gels were confirmed by Southern hybridization (FIG. 8*b*).

The amplification process may be carried out on samples obtained from either potato tubers or leaves, and the samples may be prepared by any effective means. For example, leaf samples may be prepared by obtaining a small piece of the leaf (such as a small strip from the margin of a lesion) and macerating the piece until liquid is expressed. An aliquot of expressed liquid is utilized for amplification by transfer into a PCR reaction tube. Tuber samples may be prepared by taking a small sample from a tuber, macerating the piece in an alkaline solution, such as 0.5 N NaOH, and centrifuging the macerated sample. The supernatant is diluted in buffer and an aliquot utilized for amplification by transfer into a PCR reaction tube. Alternatively, a tuber sample may be ground in water and applied to an ion exchange column which binds DNA (for example, QIAGEN Genomic-tip 20/G column). The DNA is eluted from the column according to the manufacturer's instructions, and an aliquot of eluate is utilized for amplification by transfer into a PCR reaction tube. Due to the sensitivity of the method, a preliminary step for culturing the samples in order to expand the number of microorganisms is generally unnecessary, however, this step may be added if deemed necessary. Preliminary concentration steps such as centrifugation and/or filtration may also be carried out, if desired.

Amplification is carried out according to conventional procedures well-known in the art (described by Mullis, U.S. Pat. No. 4,683,202, herein incorporated by reference). The amplified products may, then be visualized by ethidium bromide staining of agarose gels or by Southern or dot-blot hydridization techniques utilizing DNA sequences internal to the oligonucleotide primers. Effective amplification conditions are described in Example 2.

The preferred primer sets are:

1) PINF-2, 5'-CGATTCAAATGCCAAGCTAAAG-3' (SEQ ID NO: 1), and ITS3, 5'-GCATCGATGAAGAACGCAGC-3' (SEQ ID NO: 2), which amplify a DNA fragment of 456 bp from *P. infestans;*

2) PERY-2, 5'-CTGTTCCGGCGTAAGCTGG-3' (SEQ ID NO: 3), and ITS4, 5'-TCCTCCGCTTATTGATATGC-3' (SEQ ID NO: 4), which amplify a DNA fragment of 136 bp from *P. erythroseptica*; and 3) PNIC-1, 5'-ATTCAAAAGCCAAGCCACCG-3' (SEQ ID NO: 5), and ITS3, 5'-GCATCGATGAAGAACGCAGC-3' (SEQ ID NO: 2), which amplify a DNA fragment of 455 bp from *P. nicotianae*.

EXAMPLES

Example 1

Cultures and DNA sequence analysis

The origins of fungal isolates used in this experiment are listed in Table 1. Total DNA was extracted from 60 mg lyophilized fungal mycelium grown in liquid medium (pea broth) for 7 days at 18° C. in darkness using the method of Goodwin et al. (1992. *Curr. Genet.* vol. 22, pp. 107–115). Bacterial cultures were grown overnight at 27° C in LB broth without ampicillin (Sambrook et al. 1989. *Molecular Cloning: A Laboratory Manual*, 2nd ed. Cold Spring Harbor Press, Cold Spring Harbor, N.Y.). The ITS2 region of ribosomal DNA from *P. infestans* (isolates 176, 180, 550 and 561), *P. erythroseptica* (isolates 356, 357, 358, 365 and 367), *P. nicotianae* (isolates 361, 362, 363 and 364), *P. ultimum* (PY-4 and PY-5), *F. oxysporum* (FS-1) and *F. avenaceum* (FS-2) was amplified using primers ITS3 and ITS4 (White et al., supra) and cloned into the pT7Blue T-vector (Novagen, supra) following instructions provided by the manufacturer. Sequence-grade plasmid DNA was purified with Tip-100 ion exchange columns (QIAGEN, Chatsworth, Calif.). Dye-terminator cycle sequencing was performed on purified plasmid DNA using a model 373A automated DNA sequencer (Perkin-Elmer/Applied Biosystems, Inc., Foster City, Calif.) under contract with the Laboratory of Cell and Molecular Structure of the National Cancer Institute, National Institutes of Health, Frederick, Md. DNA sequences were aligned using the UW-GCG computer package on a VAX mainframe. Regions of dissimilarity among species were identified visually from multiple sequence alignments, and primers were designed and tested using standard primer criteria along with information from the PRIMER computer program (Whitehead Institute, Cambridge, Mass.). The primers were designed to be used in combination with either ITS3 or ITS4 and to produce products ranging from about 88 bp to about 537 bp.

Example 2

Polymerase Chain Reaction and Southern Hybridization

One $\mu$l of DNA (10 ng/$\mu$l) or 1 $\mu$l leaf or tuber extract, process as described under examples 4 and 5, was added to either a 24-$\mu$l reaction mixture containing 22 $\mu$M dNTPs, 0.1 $\mu$M each primer, 0.67 U Tfl DNA polymerase (Epicentre Technologies, Madison, Wis.), 1.8 mM MgCl$_2$ and PCR buffer supplied by the manufacturer or a 24-$\mu$l reaction mixture containing 22 $\mu$M dNTPs, 0.1 $\mu$M each primer, 0.5 U Taq polymerase (Perkin-Elmer, Foster City, Calif.), 1.5 mM MgCl$_2$ and 1X PCR buffer (Perkin-Elmer, supra). PCR was carried out in a Perkin Elmer Cetus model 9600 thermal cycler using a program of 94° C. for 1 min initial denaturation followed by 30 cycles of 94° C. for 15 sec, 55° C. for 15 sec and 72° C. for 15 sec, followed by a final extension of 72° C. for 6 min. PCR products were visualized by staining gels in ethidium bromide following electrophoresis on 2% agarose. HaeIII-cut ΦX174 DNA ladder (Gibco BRL, Gaithersburg, Md.) was included as a molecular weight standard.

For Southern hybridization, plasmid DNA was labeled in vitro by random priming 50 ng DNA with [$\alpha$-$^{32}$P ]dCTP (Ready-to-Go Kit, Pharmacia, Piscataway, N.J.). PCR products were electrophoresed on 2% agarose gels, and denatured and blotted onto Nytran (Micron Separations, Inc., Westboro, Mass.) nylon membranes by capillary transfer (Sambrook et al., supra). Prehybridization was carried out at 65° C. for 30 min in 0.25N NaHPP$_4$(pH 7.2)-0.25M NaCl-7% sodium dodecyl sulfate(SDS)-1 mM EDTA (Amasino, R. M. 1986. *Anal. Biochem.* vol. 152, pp. 304–307). Hybridization was performed at 65° C. for 16–20 hr, and the membranes were washed at 65° C. for 15 min in 2X SSC-0.1% SDS and twice in a 0.1X SSC-0.1% SDS solution (1X SSC=0.15M NaCl, 0.015M Na citrate). Membranes were exposed to X-ray film (Hyperfilm MP, Amersham, Arlington Heights, Ill.) and placed between intensifying screens (Lightning Plus, DuPont, Wilmington, Del.) at –80° C. for 24 to 72 hr.

Example 3

Leaf and Tuber Assays

*P. infestans*-specific primers were further tested to determine their ability to detect the pathogen in plant tissue. Both healthy and infected potato tubers and leaf tisssue were analyzed. Leaves of potato cultivar Norchip were infected with *P. infestans* following inoculation with sporangia of Mexican isolate 580. Tissue was removed from lesion margins, macerated between two glass microscope slides, and 1 $\mu$l of the liquid was pipetted into a PCR reaction tube. Tubers were inoculated with *P. infestans* by placing mycelium into wounds in the tubers and incubating at 18° C. for seven days. Using primer pair PINF2/ITS3, *P. infestans* from infected leaf tissue and from mycelium scraped from infected tubers was detected (FIG. 6). No amplification was observed from potato DNA (FIG. 6).

Example 4

Leaf Assay

The first two pairs of distal leaflets from leaves 6, 7 and 8 on 10-11-leaf plants (cultivar Norchip) were excised and placed adaxially in 150×15 mm Petri dishes lined with Parafilm and containing 1 ml of sterile distilled water. The leaves were inoculated by placing a 50-$\mu$l drop of sporangial suspension (10,000 sporangia per ml) on each leaflet. The dishes were then stacked in styrofoam trays lined with wet paper towels, placed in sealed plastic bags and incubated at 18° C. under cool white fluorescent lights. Small tissue strips (3×5 mm) were removed from margins of lesions formed seven days after inoculation and were macerated between two glass microscope slides. One microliter of the expressed liquid was pipetted into a PCR reaction tube. Amplification and visualization were carried out as described.

Example 5

Tuber Assay

Tubers were inoculated in two ways. Small pieces of mycelium from agar cultures of the *Phytophthora* species were placed into wounds cut into tubers with a sterile scalpel. The wounds were then sealed by replacing the tuber plug. Alternatively (*P. infestans* only), sporangia from 10-day-old cultures growing on Rye A medium (Caten and Jinks. 1968. *Can J. Bot.* vol. 46, pp. 329–348) were dislodged into 10 ml sterile distilled water by swabbing with a sterile bent-glass rod. Sporangia were placed at 10° C. for 3 hr to induce zoospore formation, then applied to tuber surfaces (var. Kennebec) with a micropipet. Areas of inoculation were circled with a waterproof black marker for later sampling, and the tubers were incubated in plastic bags (1 tuber per bag) at 18° C. in darkness until symptoms appeared (1–2 wk).

Two methods were used to assay potato tuber tissue for the presence of *P. infestans, P. erythroseptica* and/or *P. nicotianae* by PCR. The first method was a modification of the plant tissue technique described by Wang et al. (1993. *Nucl, Acids Res.* vol. 21, pp. 4153–4154). Ten mg of tissue were cut from tubers using a sterile scalpel, placed in 20 $\mu$l 0.5N NaOH in a 1.5 ml-microcentrifuge tube and macerated using a plastic pestle. The tubes were microfuged for 5 min to pellet the tissue, and 5 $\mu$l of supernatant was removed and immediately diluted with 45 $\mu$l 100 mM Tris, pH 8.0. The samples were then either used immediately for PCR (1 $\mu$l per 25 $\mu$l reaction) or frozen at −20° C. for later use. The above NaOH method was also used successfully with larger tuber samples (100 mg) which were macerated in 200 $\mu$l 0.5N NaOH followed by dilution in Tris buffer as described.

The second method of assaying potato tuber tissue employed a modification of the commercial QIAGEN protocol for DNA extraction from plant tissue (QIAGEN. 1995. *Genomic DNA Handbook*. QIAGEN, Inc., Chatsworth, Calif.). For this method, 100 mg of tuber tissue was macerated in 200 $\mu$l sterile distilled water in a 1.5-ml microcentrifuge tube and microfuged for 5 min. The supernatant was then applied directly to a QIAGEN Genomic-tip 20/G ion exchange column, which was treated according to manufacturer's instructions for genomic DNA isolation. Samples eluted from the column were used directly in PCR reactions and not precipitated with isopropanol as directed in the manufacturer's protocol (QIAGEN, supra).

Occasionally, visible signs of *P. infestans* (hyphae, sporangia) were present on infected potato tubers maintained at high relative humidity. To assay *P. infestans* directly by PCR, a micropipet tip (Rainin, Inc., Woburn, Mass.) was used to remove a pinhead-sized tuft of mycelium from the surface of an infected tuber. The mycelium was added directly to a PCR reaction tube (25 $\mu$l volume in a 0.5-ml tube).

Amplification and visualization were carried out as described.

We claim:

1. An oligonucleotide primer having the sequence 5'-CGATTCAAATGCCAAGCTAAAG-3' (SEQ ID NO: 1).

2. A primer set comprising oligonucleotides having the sequences 5'-CGATTCAAATGCCAAGCTAAAG-3' (SEQ ID NO: 1) and 5'-GCATCGATGAAGAACGCAGC-3' (SEQ ID NO: 2).

3. An oligonucleotide primer having the sequence 5'-CTGTTCCGGCGTAAGCTGG-3' (SEQ ID NO: 3).

4. A primer set comprising oligonucleotides having the sequences 5'-CTGTTCCGGCGTAAGCTGG-3' (SEQ ID NO: 3) and 5'-TCCTCCGCTTATTGATATGC-3' (SEQ ID NO 4).

5. An oligonucleotide primer having the sequence 5'-ATTCAAAAGCCAAGCCACCG-3' (SEQ ID NO: 5).

6. A primer set comprising oligonucleotides having the sequences 5'-ATTCAAAAGCCAAGCCACCG-3' (SEQ ID NO: 5) and 5'-GCATCGATGAAGAACGCAGC-3' (SEQ ID NO: 2).

7. A method of detecting *Phytophthora* species by polymerase chain reaction, said method comprising
   a) providing a test sample suspected of containing said *Phytophthora* or the DNA of said *Phytophthora*,
   b) amplifying the DNA of said Phythophthora with a primer set comprising oligonucleotides having the sequences 5'-CGATTCAAATGCCAAGCTAAAG-3' (SEQ ID NO: 1) and 5'-GCATCGATGAAGAACGCAGC-3' (SEQ ID NO: 2), oligonucleotides having the sequences 5'-CTGTTCCGGCGTAAGCTGG-3' (SEQ ID NO: 3) and 5'-TCCTCCGCTTATTGATATGC-3' (SEQ ID NO: 4) or oligonucleotides having the sequences 5'-ATTCAAAAGCCAAGCCACCCCG-3' (SEQ ID NO: 5) AND 5'-GCATCGATGAAGAACGCAGC-3' (SEQ ID NO: 2), and
   c) detecting the presence of amplified DNA as an indication of the presence of *Phythophthora*.

8. The method of claim 7, wherein said *Phythophthora* is *Phytophthora infestans* and the primer set comprises oligonucleotides having the sequences 5'-CGATTCAAATGCCAAGCTAAAG-3' (SEQ ID NO: 1) and 5'-GCATCGATGAAGAACGCAGC-3' (SEQ ID NO: 2).

9. The method of claim 7, wherein said *Phythophthora* is *Phytophthora erythroseptica* and the primer set comprises oligonucleotides having the sequences 5'-CTGTTCCGGCGTAAGCTGG-3' (SEQ ID NO: 3) and 5'-TCCTCCGCTTATTGATATGC-3' (SEQ ID NO: 4).

10. The method of claim 7, wherein said *Phythophthora* is *Phytophthora nicotianae* and the primer set comprises oligonucleotides having the sequences 5'-ATTCAAAAGCCAAGCCACCG-3' (SEQ ID NO: 5) and 5'-GCATCGATGAAGAACGCAGC-3' (SEQ ID NO: 2).

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Phytophthora infestans ( x i ) SEQUENCE DESCRIPTION: SEQ ID NO:1:

CGATTCAAAT GCCAAGCTAA AG 22

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Phytophthora infestans ( x i ) SEQUENCE DESCRIPTION: SEQ ID NO:2:

GCATCGATGA AGAACGCAGC 20

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Phytophthora erythroseptica (xi) SEQUENCE DESCRIPTION: SEQ ID NO:3:

CTGTTCCGGC GTAAGCTGG        19

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Phythora erythroseptica (xi) SEQUENCE DESCRIPTION: SEQ ID NO:4:

TCCTCCGCTT ATTGATATGC        20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Phytophthora nicotianae (xi) SEQUENCE DESCRIPTION: SEQ ID NO:5:

ATTCAAAAGC CAAGCCACCG        20